United States Patent [19]

Adams, Jr.

[11] 4,367,089
[45] Jan. 4, 1983

[54] FUNGICIDAL CARBAMATES OF TRIAZOLE ETHANOLS (OR ETHENOLS)

[75] Inventor: John B. Adams, Jr., Hockessin, Del.

[73] Assignee: E. I. Du Pont de Nemours and Company, Wilmington, Del.

[21] Appl. No.: 260,909

[22] Filed: May 6, 1981

Related U.S. Application Data

[63] Continuation-in-part of Ser. No. 195,085, Oct. 8, 1980, abandoned.

[51] Int. Cl.³ .................. A01N 47/18; C07D 403/12; A01N 43/64; C07D 249/08
[52] U.S. Cl. .................................... 71/76; 71/92; 424/269; 542/413; 548/262
[58] Field of Search ....................... 542/413; 548/262; 424/269; 71/92, 76

[56] References Cited

U.S. PATENT DOCUMENTS 4,237,142  12/1980  Buchel et al. .................. 424/245
4,243,405  1/1981  Balasubramanyan et al. ..... 548/262

FOREIGN PATENT DOCUMENTS 2926280  8/1981  Fed. Rep. of Germany ...... 424/269

Primary Examiner—Alton D. Rollins

[57] ABSTRACT

2-(Methoxycarbonylamino)-1H-benzimidazole-1-carboxylic acid esters such as with 1-(4-chlorophenoxy)-3,3-dimethyl-1-(1H-1,2,4-triazol-1-yl)-2-butanol are effective in controlling plant fungus diseases.

24 Claims, No Drawings

FUNGICIDAL CARBAMATES OF TRIAZOLE ETHANOLS (OR ETHENOLS)

RELATED APPLICATION

This application is a continuation-in-part of my co-pending application U.S. Ser. No. 195,085, filed Oct. 8, 1980, now abandoned.

BACKGROUND OF THE INVENTION

This invention relates to novel carbamate compounds (I), novel intermediates II and III, the use of compounds (I) and II to control fungus diseases, and the use of compounds such as (I)c both to control fungus diseases and to regulate plant growth.

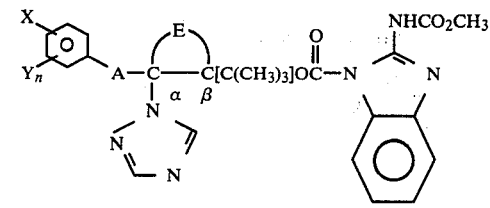

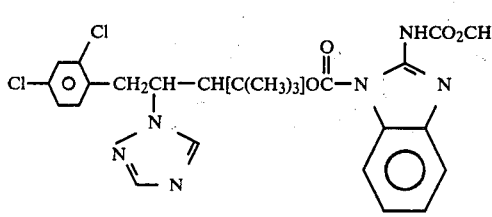

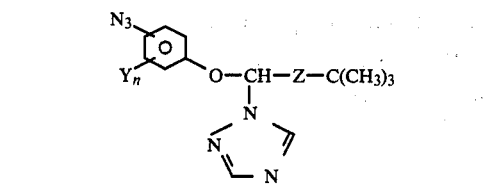

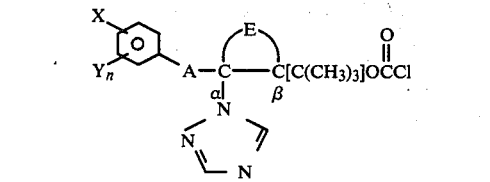

Additionally, this invention relates to fungicidal compositions containing (I) or II as active ingredient, to fungicidal and plant-growth-regulant compositions containing (I)c or relatives as active ingredient, to a method of controlling fungus diseases with compounds (I), (I)c or II, and to a method of regulating plant growth with compound (I)c and its relatives.

A number of triazole compounds are known to exhibit fungicidal activity. For example, Belgian Pat. No. 835,954 discloses compounds such as (i):

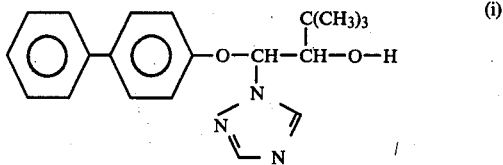

Belgian Pat. No. 857,836 discloses fungicidal triazoles such as (ii):

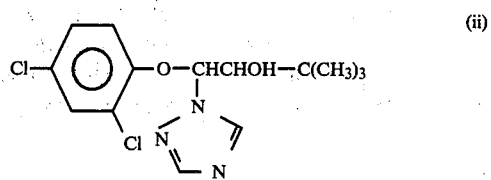

British Pat. No. 1,505,241 discloses compounds such as (iii):

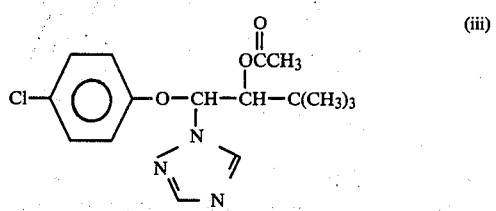

U.S. Pat. No. 3,912,752 discloses compounds such as (iv):

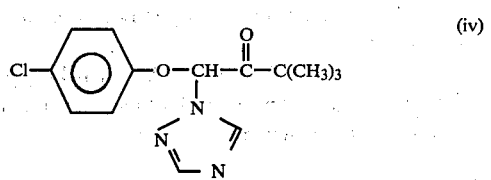

U.K. patent application GB No. 2,041,927A discloses fungicidal and plant-growth-regulant compounds such as (v):

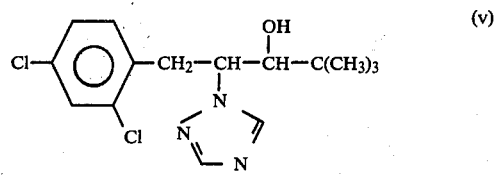

It is also known that some benzimidazole compounds exhibit fungicidal activity. For example, U.S. Pat. No. 3,657,443 discloses and claims fungicidal compounds such as (vi):

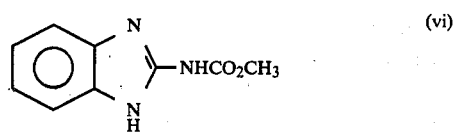

and U.S. Pat. No. 2,933,504 discloses compounds such as (vii):

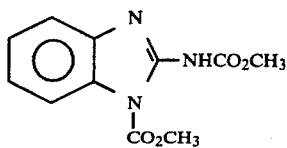

(vii)

SUMMARY OF THE INVENTION

The present invention resides in the discovery that carbamate compounds of Formula (I), and azido compounds of Formula II exhibit high fungicidal activity and that compounds within (I) wherein A is $CH_2$, e.g., (I)c, also exhibit plant-growth-regulant activity.

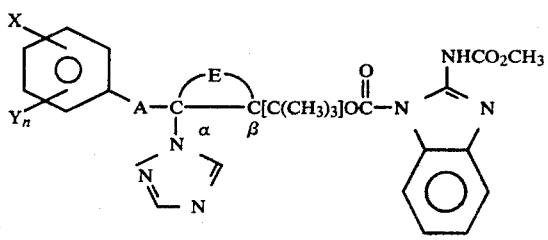

(I)

wherein
- A is O or $CH_2$;
- X is hydrogen, halogen, cyano, alkyl ($C_1$–$C_4$), alkoxy ($C_1$–$C_4$), haloalkoxy ($C_1$–$C_3$, 2–6 halogens, especially Cl and F), alkylthio ($C_1$–$C_4$), trifluoromethyl, akylsulfonyl ($C_1$–$C_4$), trifluoromethanesulfonyl, phenyl, 2- or 4-halophenyl, or azido;
- Y is halogen;
- n is 0 to 1 and can be 0 to 2 when X is halogen; and
- E is a hydrogen atom on each of carbons α and β, or can be a bond when A is oxygen.

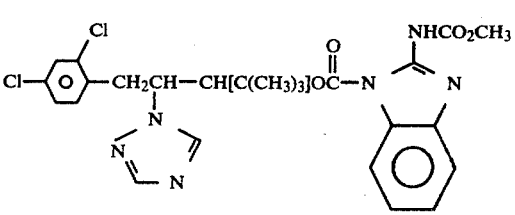

(I)c

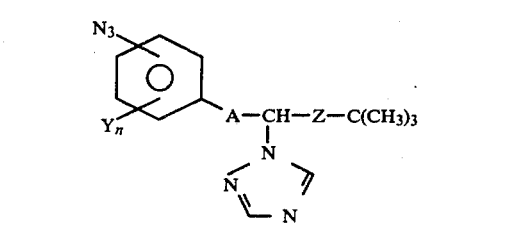

II wherein
- A is O or $CH_2$;
- Y is halogen;
- n is 0 to 1; and
- Z is C=O or CHOH.

Also included in the scope of this invention are the isomers represented by Formula (I'):

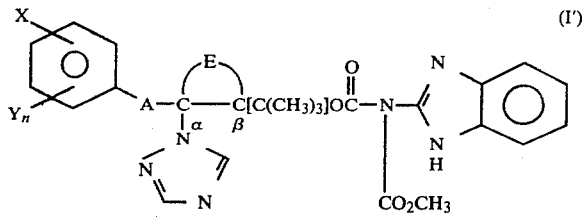

(I')

wherein A, X, Y, n and E are as defined above for compounds of Formula (I).

It should be noted that the compounds of Formula (I) include both α,β-saturated [(I)a] and α,β-unsaturated [(I)b] types:

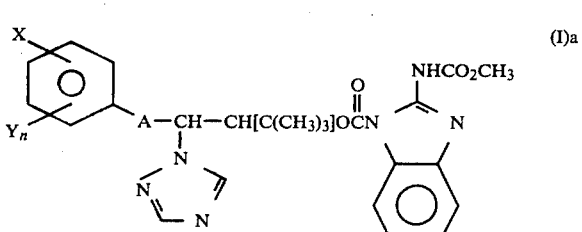

(I)a

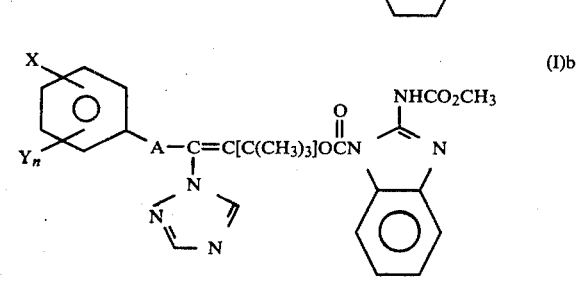

(I)b

Similarly, the isomers represented by Formula (I') contain both α,β-saturated [(I')a] and α,β-unsaturated [(I')b] types:

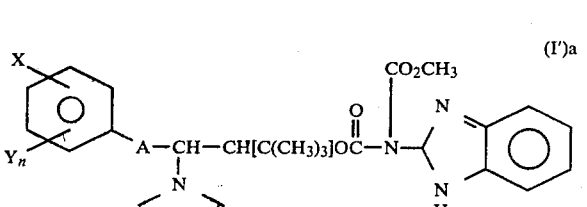

(I')a

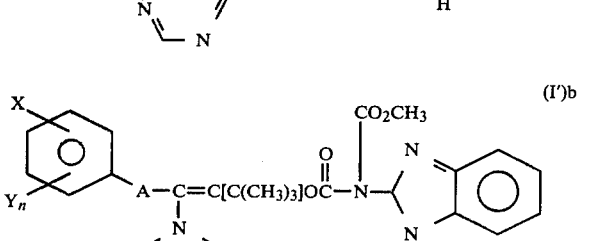

(I')b

In the compounds of Formulas (I)a, (I)b, (I')a and (I')b, the substituents are as defined for Formula (I).

Also included in the scope of this invention are the chloroformate intermediates (III), which are useful in preparing the compounds (I):

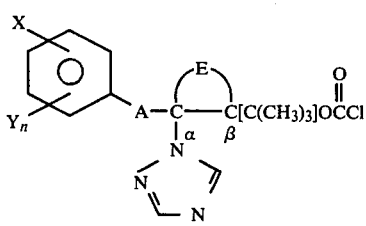

(III)

wherein the various substituents are defined as for (I).

It should be noted that the compounds of Formula III include both α,β-saturated (IIIa) and α,β-unsaturated (IIIb) types:

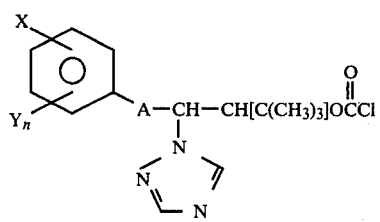

IIIa

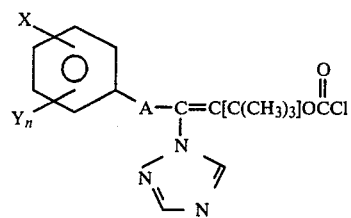

IIIb wherein the substituents are as defined for (I).

Further to this discovery are fungicidal compositions containing the compounds (I), (I') or II as active ingredient and a method of controlling fungus diseases with such compounds.

Further to this discovery are plant-growth-regulant compositions containing (I) wherein A is CH2, e.g., compound (I)c, as active ingredient and a method of controlling plant growth with those compounds.

The compounds (I), (I') and II of this invention can control a broad variety of fungal species. In fact, the compounds (I) and (I') of this invention can control some fungi which are resistant to compounds, i, ii, iii, iv, v, vi or vii.

Independently preferred for their fungicidal activity are those compounds of Formula (I) which are:

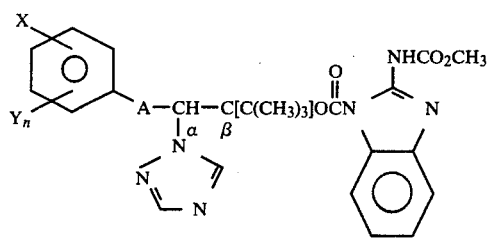

(I)a

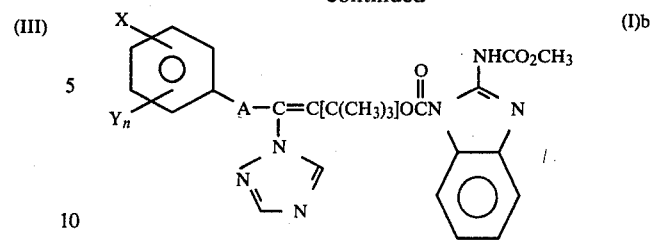

(I)b wherein X, Y, A and n are as defined for Formula (I).

Preferred for reasons of highest activity and/or lowest cost and/or ease of synthesis are those compounds of Formula (I) wherein X is hydrogen, halogen, methyl, methoxy, trifluoromethyl or phenyl.

Specifically preferred for the same reasons are those compounds of Formula (I) which are:

1-(4-chlorophenoxy)-3,3-dimethyl-1-(1H-1,2,4-triazol-1-yl)-2-butanol, ester with 2-(methoxycarbonylamino)-1H-benzimidazole-1-carboxylic acid;

1-(1,1'-biphenyl-4-yloxy)-3,3-dimethyl-1-(1H-1,2,4-triazol-1-yl)-2-butanol, ester with 2-(methoxycarbonylamino)-1H-benzimidazole-1-carboxylic acid;

1-(2,4-dichlorophenyl)-4,4-dimethyl-2-(1H-1,2,4-triazol-1-yl)-3-pentanol, ester with 2-(methoxycarbonylamino)-1H-benzimidazole-1-carboxylic acid;

1-(4-chlorophenoxy)-3,3-dimethyl-1-(1H-1,2,4-triazol-1-yl)-1-buten-2-ol, ester with 2-(methoxycarbonylamino)-1H-benzimidazole-1-carboxylic acid; and 1-(1,1'-biphenyl-4-yloxy)-3,3-dimethyl-1-(1H-1,2,4-triazol-1-yl)-1-buten-2-ol, ester with 2-(methoxycarbonylamino)-1H-benzimidazole-1-carboxylic acid.

Specifically preferred are those fungicidal intermediates of Formula II which are:

1-(4-azidophenoxy)-3,3-dimethyl-1-(1H-1,2,4-triazol-1-yl)-2-butanone; and 1-(4-azidophenoxy)-3,3-dimethyl-1-(1H-1,2,4-triazol-1-yl)-2-butanol.

Specifically preferred are those chloroformate intermediates of Formula III which are:

1-(4-chlorophenoxy)-3,3-dimethyl-1-(1H-1,2,4-triazol-1-yl)-2-butyl chloroformate;

1-(1,1'-biphenyl-4-yloxy)-3,3-dimethyl-1-(1H-1,2,4-triazol-1-yl)-2-butyl chloroformate;

1-(2,4-dichlorophenyl)-4,4-dimethyl-2-(1H-1,2,4-triazol-1-yl)-3-pentyl chloroformate;

1-(4-chlorophenoxy)-3,3-dimethyl-1-(1H-1,2,4-triazol-1-yl)-1-buten-2-yl chloroformate; and 1-(4-azidophenoxy)-3,3-dimethyl-1-(1H-1,2,4-triazol-1-yl)-2-butyl chloroformate.

DETAILED DESCRIPTION OF THE INVENTION

Preparation

The compounds of Formula (I) can be prepared by converting the appropriate alcohol (IV) or ketone (V) to the corresponding chloroformate (III), followed by reacting the chloroformate with methyl 2-benzimidazolecarbamate (V).

1(a).

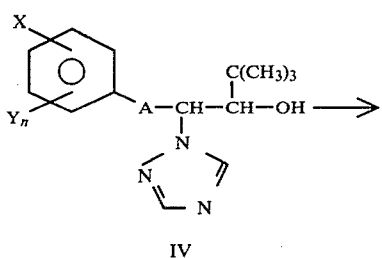

IV

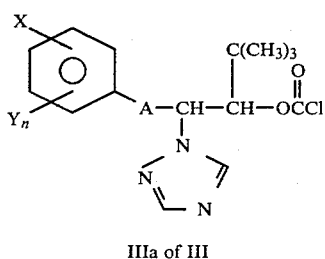

IIIa of III

1(b).

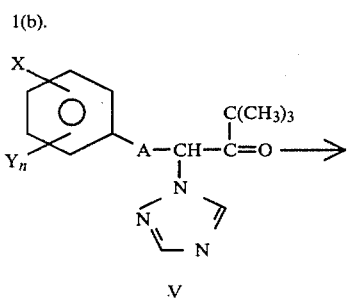

V

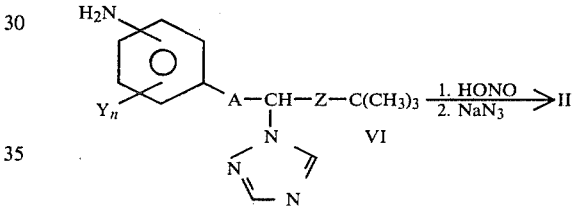

IIIb of III

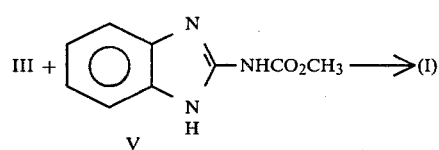

In reaction (1)a, the alcohol IV is treated with sodium hydride in an inert organic solvent (e.g., toluene, benzene or xylene), forming the sodium salt of the alcohol. The sodium salt can then react with phosgene in the same solvent, at ambient temperature up to the boiling point of the solvent, to produce the chloroformate IIIa. Alternatively, the alcohol IV can be mixed with phosgene and a base (e.g., pyridine) in the presence of an inert solvent (e.g., tetrahydrofuran, THF) at ambient temperature up to the boiling point of the solvent. Reaction time will vary with temperature; an overnight reaction period is generally sufficient at room temperature, as is about 1 hour at the boiling point in THF. Evaporation of the solvent provides a residue containing the chloroformate.

In reaction (1)b, the enol chloroformate IIIb can be prepared in substantially the same ways as described for the chloroformate IIIa. With a THF, pyridine, phosgene system, ketone V tends to provide chloroformate more slowly than does alcohol IV. Further, heating the reaction mixture is not particularly helpful in providing chloroformate IIIb. The successful preparation of enol chloroformate IIIa is surprising in view of the reported failures in attempts at preparation of enol chloroformates [e.g., R. A. Olofson et al., J. Org. Chem., 43, 752 (1978)].

In reaction 2, the chloroformate III reacts with compound V in an inert solvent (e.g., THF) in the presence of a base (e.g., pyridine) to produce the carbamate (I).

When compounds III and V react, they produce compound (I) and/or compound (I'). It is considered more likely that compound (I) alone is produced, but that is not definitely known. Thus, the present invention is intended to include both compounds (I) and (I') as they are produced.

Although many compounds within structures IV and V are known, those with X as azido (Formula II) have not been previously reported. They can be prepared by methods which are generally known, e.g., diazotization of the corresponding amino compound (VI), followed by reaction of the diazonium compound with sodium azide.

Preparation and use of the compounds of this invention are further illustrated in the examples which follow. Temperature is in °C. unless otherwise indicated.

EXAMPLE 1

Preparation of 1-(4-Chlorophenoxy)-3,3-dimethyl-1-(1H-1,2,4-triazol-1-yl)-2-butanol, ester with 2-(methoxy-carbonylamino)-1H-benzimidazole-1-carboxylic acid To a stirred, nitrogen-blanketed solution of 10 g (0.0338 mole) of 1-(4-chlorophenoxy)-3,3-dimethyl-1-(1H-1,2,4-triazol-1-yl)-2-butanol in 100 ml of toluene, was added 0.037 mole of sodium hydride in oil. After the effervescence ceased, 100 ml of a 10.9% phosgene solution in toluene was added. The mixture was heated at 85° to 95° under phosgene reflux for 2.8 hours. The excess sodium hydride was filtered off and the filtrate evaporated under reduced pressure to a residual syrup. The infrared spectrum of the syrup showed strong absorption at about 1790 cm$^{-1}$, characteristic of a chloroformate.

To the syrup was added 6.46 g of methyl 2-benzimidazolecarbamate, 30 ml of pyridine and 50 ml of methylene chloride, and the mixture was stirred for 18 hours. Then the mixture was filtered, the filtrate evaporated under reduced pressure to an oil. The oil was stirred with water and butyl chloride, the mixture filtered, and the butyl chloride layer separated and washed with 0.5 N HCl, water, and saturated brine, then dried (MgSO$_4$). The dried solution was filtered and evaporated to a residual oil. The oil was chromatographed on silica gel with chloroform. The fractions which showed a component of Rf about 0.6 on thin-layer chromatography (silica-gel-coated plates, ethyl acetate eluent) were saved, combined, and evaporated to a residual oil. Dissolution of the oil in butyl chloride, extraction of the butyl chloride solution with 4N HCl, and treatment of the acidic extract with sodium bicarbonate solution precipitated a tacky solid. The tacky solid was dissolved in butyl chloride/ethyl acetate (1/1, by volume), and the solution washed with saturated sodium bicarbonate solution, dried ($MgSO_4$), filtered, and evaporated to a viscous oil. Mass spectral analysis (with use of a Vespel ® tip) showed a molecular ion (m/e 513) corresponding to 1-(4-chlorophenoxy)-3,3-dimethyl-1-(1H-1,2,4-triazol-1-yl)-2-butanol, ester with 2-(methoxycarbonylamino)-1H-benzimidazole-1-carboxylic acid.

EXAMPLE 2

Preparation of 1-(4-Chlorophenoxy)-3,3-dimethyl-1-(1H-1,2,4-triazol-1-yl)-2-butanol, ester with 2-(methoxycarbonylamino)-1H-benzimidazole-1-carboxylic acid, Alternate Method To a solution of 29.6 g (0.1 mole) of 1-(4-chlorophenoxy)-3,3-dimethyl-1-(1H-1,2,4-triazol-1-yl)-2-butanol in 250 ml of THF was added 20 ml of liquid phosgene, followed by 9 ml of pyridine. The mixture was stirred at ambient temperature for about 21 hours. White solid (water-soluble) was filtered off and the THF filtrate concentrated in vacuum to a residual oil, the intermediate chloroformate. Further purification of the chloroformate was accomplished by dissolving it in about 300 ml of 1-chlorobutane, washing the butyl chloride solution with 0.5 N HCl (twice), water and saturated brine, drying ($MgSO_4$), filtration, and evaporation of the filtrate in vacuum to leave, as a residual oil, 1-(4-chlorophenoxy)-3,3-dimethyl-1-(1H-1,2,4-triazol-2-yl)-2-butyl chloroformate.

To a solution of the chloroformate in 250 ml of THF was added 19.1 g (0.1 mole) of methyl 2-benzimidazolecarbamate and 9 ml of pyridine. The mixture was stirred for 22 hours, filtered, and the filtrate evaporated in vacuum to a residual syrup. The syrup was dissolved in 500 ml of 1-chlorobutane, the turbid solution filtered, and the filtrate washed with 1N HCl (twice), water, and saturated brine, then dried ($MgSO_4$), and the mixture filtered and evaporated in vacuum to a residual syrup. The syrup was dissolved in 130 ml of benzene, the solution frozen, and the benzene removed by sublimation in vacuum. This operation left 44.1 g (about 86% overall yield) of 1-(4-chlorophenoxy)-3,3-dimethyl-1-(1H-1,2,4-triazol-1-yl)-2-butanol, ester with 2-(methoxycarbonylamino)-1H-benzimidazole-1-carboxylic acid as a white powder, m.p. ca. 75–80°.

EXAMPLE 3

Preparation of 1-(1,1'-Biphenyl-4-yloxy)-3,3-dimethyl-1-(1H-1,2,4-triazol-1-yl)-2-butanol, ester with 2-(methoxycarbonylamino)-1H-benzimidazole-1-carboxylic acid To a solution of 3.35 g (0.01 mole) of 1-(1,1'-biphenyl-4-yloxy)-3,3-dimethyl-1-(1H-1,2,4-triazol-1-yl)-2-butanol in 25 ml of THF was added 2.7 ml of liquid phosgene, followed in a few minutes by 0.9 ml of pyridine. The mixture was boiled under reflux for 1 hour. The solid (water-soluble) was filtered off and the filtrate evaporated in vacuum to a foamy residue. The residue was dissolved in 1-chlorobutane and the solution washed with 0.5 N HCl (three times), water, and saturated brine, then dried ($MgSO_4$), and the mixture filtered and evaporated in vacuum to an oil, which is 1-(1,1'-biphenyl-4-yloxy)-3,3-dimethyl-1-(1H-1,2,4-triazol-1-yl)-2-butyl chloroformate. It showed the characteristic absorption in the infrared spectrum at about 1780–1820 $cm^{-1}$.

To a solution of the chloroformate in 25 ml of THF was added 1.91 g (0.01 mole) of methyl 2-benzimidazolecarbamate and 0.9 ml of pyridine. The mixture was stirred for 16 hours, filtered, and the filtrate evaporated in vacuum to a foamy residue. The residue was dissolved in 1-chlorobutane and the solution washed with 1 N HCl (three times), water, and saturated brine, then dried ($MgSO_4$), the mixture filtered, and the filtrate cooled to precipitate white solid, isolated by filtration. This solid is 1-(1,1'-biphenyl-4-yloxy)-3,3-dimethyl-1-(1H-1,2,4-triazol-1-yl)-2-butanol, ester with 2-(methoxycarbonylamino)-1H-benzimidazole-1-carboxylic acid. It exhibits a m.p. of 186°–188°. Mass spectral analysis (with use of a Vespel ® tip) showed a molecular ion (m/e 554) corresponding to this carbamate.

Anal. Calcd. for $C_{30}H_{30}N_6O_5$: C, 65.0; H, 5.5; N, 15.2%. Anal. Found: C, 65.0; H, 5.4; N, 15.0%.

EXAMPLE 4

Preparation of 1-(2,4-Dichlorophenyl)-4,4-dimethyl-2-(1H-1,2,4-triazol-1-yl)-3-pentanol, ester with 2-(methoxycarbonylamino)-1H-benzimidazole-1-carboxylic acid To a solution of 3.28 g (0.01 mole) of 1-(2,4-dichlorophenyl)-4,4-dimethyl-2-(1H-1,2,4-triazol-1-yl)-3-pentanol in 25 ml of THF was added 2.5 ml of liquid phosgene, followed by 0.85 ml of pyridine. The mixture was boiled under reflux for 1 hour, then filtered, and the filtrate evaporated in vacuum to an off-white solid foam. The foam was dissolved in 1-chlorobutane, a little insoluble residue filtered off, and th 1-chlorobutane filtrate washed with 0.5 N HCl (twice), water, and saturated brine. The dried ($MgSO_4$) butyl chloride solution was filtered and evaporated in vacuum to an off-white solid foam, 1-(2,4-dichlorophenyl)-4,4-dimethyl-2-(1H-1,2,4-triazol-1-yl)-3-pentyl chloroformate. The infrared spectrum showed the expected absorption at ca. 1825 $cm^{-1}$.

To a solution of the chloroformate in 25 ml of THF was added 1.91 g (0.01 mole) of methyl 2-benzimidazolecarbamate and 0.9 ml of pyridine. After 16.5 hrs. the mixture was filtered and the filtrate evaporated in vacuum to a solid foam. The foam was dissolved in 1-chlorobutane and the solution washed with 1 N HCl (twice), water, and saturated brine. The dried ($MgSO_4$) butyl chloride solution was evaporated to provide 1-(2,4-dichlorophenyl)-4,4-dimethyl-2-(1H-1,2,4-triazol-1-yl)-3-pentanol, ester with 2-(methoxycarbonylamino)-1H-benzimidazole-1-carboxylic acid as a solid foam, m.p. about 87°–92°, with earlier shrinking. Mass spectral analysis (with use of a Vespel ® tip) showed a molecular ion (m/e 544; 2Cl) corresponding to this carbamate.

EXAMPLE 5

Preparation of 1-(4-Chlorophenoxy)-3,3-dimethyl-1-(1H-1,2,4-triazol-1-yl)-1-buten-2-ol, ester with 2-(methoxycarbonylamino)-1H-benzimidazole-1-carboxylic acid To a solution of 29.4 g (0.01 mole) of 1-(4-chlorophenoxy)-3,3-dimethyl-1-(1H-1,2,4-triazol-1-yl)-2-butanone in 250 ml of THF was added 20 ml of liquid phosgene, followed by 9 ml of pyridine. After 3 days, the mixture was filtered and the filtrate evaporated in vacuum to a residual oil. The oil was dissolved in hot 1-chlorobutane and the solution filtered to remove a little white solid. The filtrate was cooled, precipitating a white solid. The solid was isolated by filtration, providing 12.9 g (36% of theoretical) of 1-(4-chlorophenoxy)-3,3-dimethyl-1-(1H-1,2,4-triazol-1-yl)-1-buten-2-yl chloroformate, m.p. 159°–161°. The infrared spectrum showed absorption at ca 1800 cm$^{-1}$.

Anal. Calcd. for $C_{15}H_{15}Cl_2N_3O_3$: C, 50.6; H, 4.2; Cl, 19.9; N, 11.8%. Anal. Found: C, 50.2; H, 4.4; Cl, 19.4; N, 11.8%.

The chloroformate was also prepared by sequential reaction of the ketone with sodium hydride in toluene at reflux, followed by reaction with excess phosgene in the same solvent during a 40-minute period.

To a solution of about 0.01 mole of the chloroformate in 25 ml of THF was added 1.91 g (0.01 mole) of methyl 2-benzimidazolecarbamate and an excess of powdered potassium carbonate, and the mixture stirred for 15 hours, then filtered. The filtrate was evaporated in vacuum to an oil. The oil was dissolved in 1-chlorobutane, a small amount of solid filtered off, and the filtrate evaporated in vacuum to an oil. The oil was crystallized from cyclohexane, providing 1-(4-chlorophenoxy)-3,3-dimethyl-1-(1H-1,2,4-triazol-1-yl)-1-buten-2-ol, ester with 2-(methoxycarbonylamino)-1H-benzimidazole-1-carboxylic acid as a white solid, m.p. about 58–75° (poorly defined). Mass spectral analysis (with use of a Vespel ® tip) showed a molecular ion (m/e 511) corresponding to this carbamate.

EXAMPLE 6

Preparation of 1-(4-Azidophenoxy)-3,3-dimethyl-1-(1H-1,2,4-triazol-1-yl)-2-butanol, ester with 2-(methoxycarbonylamino)-1H-benzimidazole-1-carboxylic acid To a solution of 2.13 g (0.0075 mole) of 1-(4-azidophenoxy)-3,3-dimethyl-1-(1H-1,2,4-triazol-1-yl)-2-butanol in 25 ml of THF was added 2.2 ml of liquid phosgene, followed by 0.7 ml of pyridine. The mixture was boiled under reflux for 1 hour, then filtered and the filtrate evaporated to an oil. The oil was dissolved in 1-chlorobutane and the butyl chloride solution washed with 1 N HCl, water, and saturated brine, dried (MgSO$_4$), and the solution evaporated to an oil, which is 1-(4-azidophenoxy)-3,3-dimethyl-1-(1H-1,2,4-triazol-1-yl)-2-butyl chloroformate. The infrared spectrum shows the expected absorption ca 1810 cm$^{-1}$ (chloroformate carbonyl) and 2120 cm$^{-1}$ (azido).

The chloroformate was dissolved in 25 ml of THF, 1.30 g of methyl 2-benzimidazolecarbamate and 0.6 ml of pyridine were added and the mixture stirred for 17 hours, then filtered. The filtrate was evaporated to a residual foamy syrup, in vacuum. The syrup was dissolved in butyl chloride and chromatographed on silica gel in the same solvent, providing (after evaporation of the solvent in vacuum) an oil that was substantially homogeneous on thin-layer chromatography (on silica gel, with chloroform/ethyl acetate, 1/1, v/v; Rf ca. 0.45). The oil was dissolved in benzene, the solution frozen, and the benzene removed by sublimation in vacuum, leaving 1-(4-azidophenoxy)-3,3-dimethyl-1-(1H-1,2,4-triazol-1-yl)-2-butanol, ester with 2-(methoxycarbonylamino)-1H-benzimidazole-1-carboxylic acid as a pale-yellow powder, m.p. ca. 79° (poorly defined; product shrinks in 60's°C.). Mass spectral analysis of the product (with use of a Vespel ® tip) showed a molecular ion (m/e 519) corresponding to this carbamate.

EXAMPLE 7

Preparation of 1-(4-Azidophenoxy)-3,3-dimethyl-1-(1H-1,2,4-triazol-1-yl)-2-butanone To 188.8 g (0.6883 mole) of 1-(4-aminophenoxy)-3,3-dimethyl-1-(1H-1,2,4-triazole-1-yl)-2-butanone was added a solution of 155 ml of concentrated hydrochloric acid in 276 ml of water. The resulting solution was cooled to 0–5° and a solution of 49.9 g of sodium nitrite in 172 ml of water was added during a 32-minute period. After an additional 45 minutes at the same temperature, a solution of 46.2 g of sodium azide in 345 ml of water was added during a 15-minute period; the temperature was kept down to about 20° during the exothermic reaction. A thick oil separated during the addition of sodium azide; it solidified soon after all the sodium azide was added.

After an additional hour the solid was filtered off and washed well with water. The damp cake was dissolved in about 1200 ml of boiling 1-chlorobutane, the water drawn off, and the butyl chloride solution washed with warm water and saturated sodium bicarbonate solution. The dried (MgSO$_4$) solution was boiled down to 800 ml, diluted to 1600 ml with hexane, cooled to 10° and the product, 1-(4-azidophenoxy)-3,3-dimethyl-1-(1H-1,2,4-triazol-1-yl)-2-butanone, obtained as a buff-colored solid by filtration. Yield; 196.7 g (95% of theoretical). Additional product was recovered from the filtrate by evaporation, raising the yield to over 98% of theoretical. The product exhibited a m.p. of 108–109°.

Anal. Calcd. for $C_{14}H_{16}N_6O_2$: C, 56.0; H, 5.4; N, 28.0%. Anal. Found: C, 55.8; H, 5.2; N, 28.0%.

IR: absorption at ca. 2120 cm$^{-1}$ (azido), 1720 cm$^{-1}$ (ketone).

EXAMPLE 8

Preparation of 1-(4-Azidophenoxy)-3,3-dimethyl-1-(1H-1,2,4-triazol-1-yl)-2-butanol A stirred solution of 21.8 (0.790 of 1-(4-aminophenoxy)-3,3-dimethyl-1-(1H-1,2,4-triazol-1-yl)-2- butanol in 31.7 ml of water and 17.8 ml of concentrated hydrochloric acid was cooled to 0° to 5°. A solution of 5.73 g of sodium nitrite in 19.8 ml of water was added over a 15-minute period, and the mixture stirred for an additional 33 minutes, all at 0° to 5°. Then a solution of 5.3 g of sodium azide in 40 ml of water was dripped in during a 10 minute period, with foaming and precipitation of gum, the temperature being allowed to rise to 8° during the addition and to 20° during the next 20 minutes.

The mixture was diluted with water and twice extracted with butyl chloride. The combined butyl chloride extracts were washed twice with water, with saturated sodium bicarbonate solution, the dried (MgSO$_4$). After warming and filtration, the solution was concentrated to 1000 ml under reduced pressure, cooled, and diluted with 40 ml of hexane, precipitating 1-(4-azidophenoxy-3,3-dimethyl-1-(1H-1,2,4-triazol-1-yl)-2-butanol as a buff-colored solid. The solid was isolated by filtration. It exhibited a m.p. of 122–125°. Yield: 16.1 g (75% of theoretical). Additional product was recoverable from the filtrate.

Anal. Calcd. for $C_{14}H_{18}N_6O_2$: C, 55.6; H, 6.0; N, 27.8%. Found: C, 55.8; H, 6.0; N, 27.0%.

By use of the appropriate alcohol starting material and the methods described in Examples 1, 2, 3, 4 or 6, the compounds of Tables 1a and 2a can be prepared.

By use of the appropriate ketone starting material and the methods described in Example 5, the compounds of Tables 1b and 2b can be prepared.

These tables are to be considered as exemplary, not limiting.

TABLE 1a

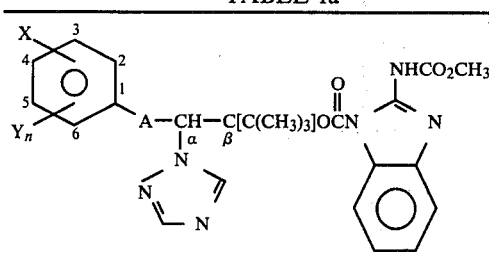

(I)a

| A | X | Y | n |
|---|---|---|---|
| O | H | — | 0 |
| O | 4-Br | — | 0 |
| O | 4-I | — | 0 |
| O | 4-F | — | 0 |
| O | 4-NC— | — | 0 |
| O | 4-CH$_3$ | — | 0 |
| O | 4-(CH$_3$)$_3$C | — | 0 |
| O | 4-CH$_3$O | — | 0 |
| O | 4-(CH$_3$)$_3$CO | — | 0 |
| O | 4-CF$_3$O | — | 0 |
| O | 4-CF$_2$HCF$_2$O | — | 0 |
| O | 4-CFClHCF$_2$O | — | 0 |
| O | 4-CFBrHCF$_2$O | — | 0 |
| O | 4-CF$_3$CHFCF$_2$O | — | 0 |
| O | 4-CF$_2$HO | — | 0 |
| O | 4-CF$_3$CH$_2$O | — | 0 |
| O | 4-CH$_3$S | — | 0 |
| O | 4-(CH$_3$)$_3$CS | — | 0 |
| O | 4-CF$_3$ | — | 0 |
| O | 4-CH$_3$SO$_2$ | — | 0 |
| O | 4-CH$_3$(CH$_2$)$_3$SO$_2$ | — | 0 |
| O | 4-CF$_3$SO$_2$ | — | 0 |
| O | 4-C$_6$H$_5$ | — | 0 |
| O | 4-(4-Cl-C$_6$H$_4$) | — | 0 |
| O | 4-(3-Cl-C$_6$H$_4$) | — | 0 |
| O | 2-Cl | 4-Cl | 1 |
| O | 2-Cl | — | 0 |
| O | 2-Cl | 6-Cl | 1 |
| O | 2-CH$_3$ | 4-Cl | 1 |
| O | 2-Cl | 5-Cl | 1 |
| O | 2-Cl | 4,5-Di—Cl | 2 |
| O | 2-CH$_3$ | 5-Cl | 1 |
| O | 3-CH$_3$ | 4-Cl | 1 |
| O | 5-N$_3$ | 2-Cl | 1 |
| CH$_2$ | H | — | 0 |
| CH$_2$ | 4-Br | — | 0 |
| CH$_2$ | 4-I | — | 0 |
| CH$_2$ | 4-F | — | 0 |
| CH$_2$ | 4-NC | — | 0 |
| CH$_2$ | 4-CH$_3$ | — | 0 |
| CH$_2$ | 4-(CH$_3$)$_3$C | — | 0 |
| CH$_2$ | 4-CH$_3$O | — | 0 |

TABLE 1a-continued

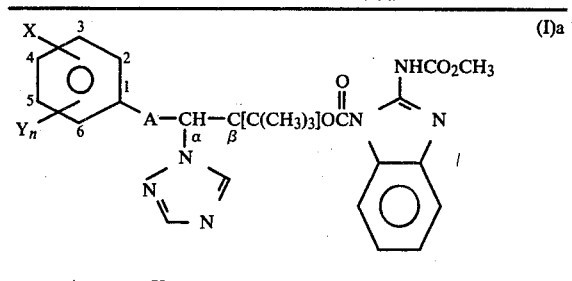

(I)a

| A | X | Y | n |
|---|---|---|---|
| CH$_2$ | 4-(CH$_3$)$_3$CO | — | 0 |
| CH$_2$ | 4-CF$_3$O | — | 0 |
| CH$_2$ | 4-CF$_2$HCF$_2$O | — | 0 |
| CH$_2$ | 4-CF$_3$CHFCF$_2$O | — | 0 |
| CH$_2$ | 4-CF$_2$HO | — | 0 |
| CH$_2$ | 4-CF$_3$CH$_2$O | — | 0 |
| CH$_2$ | 4-CH$_3$S | — | 0 |
| CH$_2$ | 4-(CH$_3$)$_3$CS | — | 0 |
| CH$_2$ | 4-CF$_3$ | — | 0 |
| CH$_2$ | 4-CH$_3$SO$_2$ | — | 0 |
| CH$_2$ | 4-CH$_3$(CH$_2$)$_3$SO$_2$ | — | 0 |
| CH$_2$ | 4-CF$_3$SO$_2$ | — | 0 |
| CH$_2$ | 4-C$_6$H$_5$ | — | 0 |
| CH$_2$ | 4-N$_3$ | — | 0 |
| CH$_2$ | 4-Cl | 3-Cl | 1 |
| CH$_2$ | 2-F | — | 0 |
| CH$_2$ | 2-Cl | 4-Cl | 1 |
| CH$_2$ | 2-Cl | — | 0 |
| CH$_2$ | 3-F | — | 0 |
| CH$_2$ | 3-Br | — | 0 |
| CH$_2$ | 2-Cl | 6-Cl | 1 |
| CH$_2$ | 2-Cl | 4,5-Di—Cl | 2 |
| CH$_2$ | 2-Cl | 3,6-Di—Cl | 2 |
| CH$_2$ | 2-F | 4-Cl | 1 |
| CH$_2$ | 2-F | 4-F | 1 |
| CH$_2$ | 2-Br | 4-Br | 1 |
| CH$_2$ | 2-CH$_3$O | — | 0 |
| CH$_2$ | 2-CH$_3$ | — | 0 |
| CH$_2$ | 3-Cl | — | 0 |
| CH$_2$ | 2-CH$_3$O | 5-Br | 1 |
| CH$_2$ | 4-C$_2$H$_5$O | — | 0 |
| CH$_2$ | 2-C$_2$H$_5$O | — | 0 |
| CH$_2$ | 2-I | — | 0 |
| CH$_2$ | 4-CH$_3$O | 3-Cl | 1 |
| CH$_2$ | 2-Cl | 6-F | 1 |
| CH$_2$ | 3-CH$_3$ | — | 0 |
| CH$_2$ | 4-C$_2$H$_5$ | — | 0 |
| CH$_2$ | 2-Cl | 4-F | 1 |
| CH$_2$ | 3-C$_2$H$_5$O | — | 0 |
| CH$_2$ | (CH$_3$)$_2$CH | — | 0 |

TABLE 1b

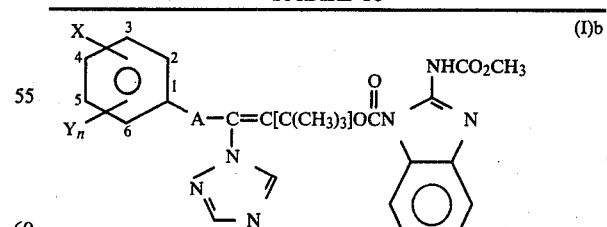

(I)b

| A | X | Y | n |
|---|---|---|---|
| O | H | — | 0 |
| O | 4-Br | — | 0 |
| O | 4-I | — | 0 |
| O | 4-F | — | 0 |
| O | 4-NC— | — | 0 |
| O | 4-CH$_3$ | — | 0 |
| O | 4-(CH$_3$)$_3$C | — | 0 |

TABLE 1b-continued

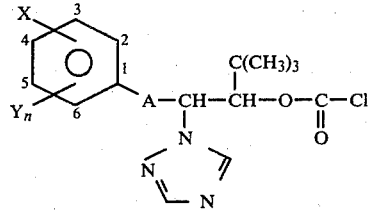

(I)b

| A | X | Y | n |
|---|---|---|---|
| O | 4-CH₃O | — | 0 |
| O | 4-(CH₃)₃CO | — | 0 |
| O | 4-CF₃O | — | 0 |
| O | 4-CF₂HCF₂O | — | 0 |
| O | 4-CFClHCF₂O | — | 0 |
| O | 4-CFBrHCF₂O | — | 0 |
| O | 4-CF₃CHFCF₂O | — | 0 |
| O | 4-CF₂HO | — | 0 |
| O | 4-CF₃CH₂O | — | 0 |
| O | 4-CH₃S | — | 0 |
| O | 4-(CH₃)₃CS | — | 0 |
| O | 4-CF₃ | — | 0 |
| O | 4-CH₃SO₂ | — | 0 |
| O | 4-CH₃(CH₂)₃SO₂ | — | 0 |
| O | 4-CF₃SO₂ | — | 0 |
| O | 4-⟨phenyl⟩ | — | 0 |
| O | 4-Cl-⟨phenyl⟩ | — | 0 |
| O | 4-⟨phenyl-Cl⟩ | — | 0 |
| O | 2-Cl | 4-Cl | 1 |
| O | 2-Cl | — | 0 |
| O | 2-Cl | 6-Cl | 1 |
| O | 2-CH₃ | 4-Cl | 1 |
| O | 2-Cl | 5-Cl | 1 |
| O | 2-Cl | 4,5-Di—Cl | 2 |
| O | 2-CH₃ | 5-Cl | 1 |
| O | 3-CH₃ | 4-Cl | 1 |
| O | 5-N₃ | 2-Cl | 1 |

TABLE 2a

Structure with A-CH-CH(C(CH₃)₃)-O-C(=O)-Cl and imidazole N

| A | X | Y | n |
|---|---|---|---|
| O | H | — | 0 |
| O | 4-Br | — | 0 |
| O | 4-I | — | 0 |
| O | 4-F | — | 0 |
| O | 4-NC— | — | 0 |
| O | 4-CH₃ | — | 0 |
| O | 4-(CH₃)₃C | — | 0 |
| O | 4-CH₃O | — | 0 |
| O | 4-(CH₃)₃CO | — | 0 |
| O | 4-CF₃O | — | 0 |
| O | 4-CF₂HCF₂O | — | 0 |
| O | 4-CFClHCF₂O | — | 0 |
| O | 4-CFBrHCF₂O | — | 0 |

TABLE 2a-continued

| A | X | Y | n |
|---|---|---|---|
| O | 4-CF₃CHFCF₂O | — | 0 |
| O | 4-CF₂HO | — | 0 |
| O | 4-CF₃CH₂O | — | 0 |
| O | 4-CH₃S | — | 0 |
| O | 4-(CH₃)₃CS | — | 0 |
| O | 4-CF₃ | — | 0 |
| O | 4-CH₃SO₂ | — | 0 |
| O | 4-CH₃(CH₂)₃SO₂ | — | 0 |
| O | 4-CF₃SO₂ | — | 0 |
| O | 4-⟨phenyl⟩ | — | 0 |
| O | 4-Cl-⟨phenyl⟩ | — | 0 |
| O | 4-⟨phenyl-Cl⟩ | — | 0 |
| O | 2-Cl | 4-Cl | 1 |
| O | 2-Cl | — | 0 |
| O | 2-Cl | 6-Cl | 1 |
| O | 2-CH₃ | 4-Cl | 1 |
| O | 2-Cl | 5-Cl | 1 |
| O | 2-Cl | 4,5-Di—Cl | 2 |
| O | 2-CH₃ | 5-Cl | 1 |
| O | 3-CH₃ | 4-Cl | 1 |
| O | 5-N₃ | 2-Cl | 1 |
| CH₂ | H | — | 0 |
| CH₂ | 4-Br | — | 0 |
| CH₂ | 4-I | — | 0 |
| CH₂ | 4-F | — | 0 |
| CH₂ | 4-NC | — | 0 |
| CH₂ | 4-CH₃ | — | 0 |
| CH₂ | 4-(CH₃)₃C | — | 0 |
| CH₂ | 4-CH₃O | — | 0 |
| CH₂ | 4-(CH₃)₃CO | — | 0 |
| CH₂ | 4-CF₃O | — | 0 |
| CH₂ | 4-CF₂HCF₂O | — | 0 |
| CH₂ | 4-CF₃CHFCF₂O | — | 0 |
| CH₂ | 4-CF₂HO | — | 0 |
| CH₂ | 4-CF₃CH₂O | — | 0 |
| CH₂ | 4-CH₃S | — | 0 |
| CH₂ | 4-(CH₃)₃CS | — | 0 |
| CH₂ | 4-CF₃ | — | 0 |
| CH₂ | 4-CH₃SO₂ | — | 0 |
| CH₂ | 4-CH₃(CH₂)₃SO₂ | — | 0 |
| CH₂ | 4-CF₃SO₂ | — | 0 |
| CH₂ | 4-⟨phenyl⟩ | — | 0 |
| CH₂ | 4-N₃ | — | 0 |
| CH₂ | 4-Cl | 3-Cl | 1 |
| CH₂ | 2-F | — | 0 |
| CH₂ | 2-Cl | 4-Cl | 1 |
| CH₂ | 2-Cl | — | 0 |
| CH₂ | 3-F | — | 0 |
| CH₂ | 3-Br | — | 0 |
| CH₂ | 2-Cl | 6-Cl | 1 |
| CH₂ | 2-Cl | 4,5-Di—Cl | 2 |
| CH₂ | 2-Cl | 3,6-Di—Cl | 2 |
| CH₂ | 2-F | 4-Cl | 1 |
| CH₂ | 2-F | 4-F | 1 |

TABLE 2a-continued

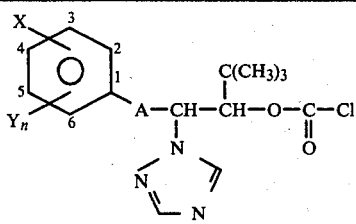

| A | X | Y | n |
|---|---|---|---|
| CH₂ | 2-Br | 4-Br | 1 |
| CH₂ | 2-CH₃O | — | 0 |
| CH₂ | 2-CH₃ | — | 0 |
| CH₂ | 3-Cl | — | 0 |
| CH₂ | 2-CH₃O | 5-Br | 1 |
| CH₂ | 4-C₂H₅O | — | 0 |
| CH₂ | 2-C₂H₅O | — | 0 |
| CH₂ | 2-I | — | 0 |
| CH₂ | 4-CH₃O | 3-Cl | 1 |
| CH₂ | 2-Cl | 6-F | 1 |
| CH₂ | 3-CH₃ | — | 0 |
| CH₂ | 4-C₂H₅ | — | 0 |
| CH₂ | 2-Cl | 4-F | 1 |
| CH₂ | 3-C₂H₅O | — | 0 |
| CH₂ | (CH₃)₂CH | — | 0 |

TABLE 2b

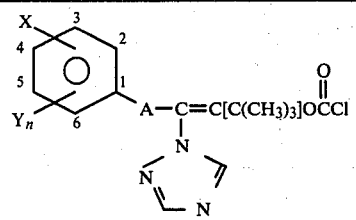

| A | X | Y | n |
|---|---|---|---|
| O | H | — | 0 |
| O | 4-Br | — | 0 |
| O | 4-I | — | 0 |
| O | 4-F | — | 0 |
| O | 4-NC— | — | 0 |
| O | 4-CH₃ | — | 0 |
| O | 4-(CH₃)₃C | — | 0 |
| O | 4-CH₃O | — | 0 |
| O | 4-(CH₃)₃CO | — | 0 |
| O | 4-CF₃O | — | 0 |
| O | 4-CF₂HCF₂O | — | 0 |
| O | 4-CFClHCF₂O | — | 0 |
| O | 4-CFBrHCF₂O | — | 0 |
| O | 4-CF₃CHFCF₂O | — | 0 |
| O | 4-CF₂HO | — | 0 |
| O | 4-CF₃CH₂O | — | 0 |
| O | 4-CH₃S | — | 0 |
| O | 4-(CH₃)₃CS | — | 0 |
| O | 4-CF₃ | — | 0 |
| O | 4-CH₃SO₂ | — | 0 |
| O | 4-CH₃(CH₂)₃SO₂ | — | 0 |
| O | 4-CF₃SO₂ | — | 0 |
| O | 4-(C₆H₅O)— | — | 0 |
| O | 4-Cl-(C₆H₄O)— | — | 0 |
| O | 4-(2-Cl-C₆H₄O)— | — | 0 |
| O | 2-Cl | 4-Cl | 1 |

TABLE 2b-continued

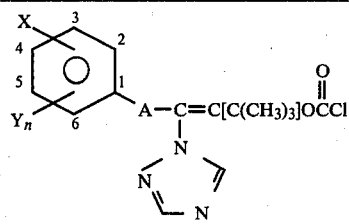

| A | X | Y | n |
|---|---|---|---|
| O | 2-Cl | — | 0 |
| O | 2-Cl | 6-Cl | 1 |
| O | 2-CH₃ | 4-Cl | 1 |
| O | 2-Cl | 5-Cl | 1 |
| O | 2-Cl | 4,5-Di—Cl | 2 |
| O | 2-CH₃ | 5-Cl | 1 |
| O | 3-CH₃ | 4-Cl | 1 |
| O | 5-N₃ | 2-Cl | 1 |

Formulations

Useful formulations of the compounds of Formulae (I) and II can be prepared in conventional ways. For example, the compounds can be formulated as dusts, granules, pellets, solutions, suspensions, emulsions, wettable powders, emulsifiable concentrates and the like. Many of these may be applied directly. Sprayable formulations can be extended in suitable media and used at spray volumes of from a few liters to several hundred liters per hectare. High-strength compositions are primarily used as intermediates for further formulation. The formulations, broadly, can contain from about 0.1% to 99% by weight of active ingredient(s) and at least one of (a) about 0.1% to 20% surfactant(s) and (b) about 1% to 99.9% solid or liquid inert diluent(s). Ordinarily, useful formulations will contain these ingredients in the following approximate proportions as shown in Table 3.

TABLE 3

| | Active Ingredient | Weight Percent* Diluent(s) | Surfactant(s) |
|---|---|---|---|
| Wettable Powders | 20–90 | 0–74 | 1–10 |
| Oil Suspensions, Emulsions, Solutions, (including Emulsifiable Concentrates) | 3–50 | 40–95 | 0–15 |
| Aqueous Suspension | 10–50 | 40–84 | 1–20 |
| Dusts | 1–25 | 70–99 | 0–5 |
| Granules and Pellets | 0.1–95 | 5–99.9 | 0–15 |
| High-strength Compositions | 90–99 | 0–10 | 0–2 |

*Active ingredient plus at least one of a Surfactant or a Diluent equals 100 weight percent.

Lower or higher levels of active ingredient can be present depending on the intended use and the physical properties of the compound. Higher ratios of surfactant to active ingredient are sometimes desirable, and are achieved by incorporation into the formulation or by tank mixing.

Some typical solid diluents are described in Watkins, et al., "Handbook of Insecticide Dust Diluents and Carriers", 2nd Ed., Dorland Books, Caldwell, New Jersey, but other solids, either mined or manufactured, may be used. The more absorptive diluents are preferred for wettable powders and the denser ones for dusts. Typical liquid diluents and solvents are described in Marsden, "Solvents Guide," 2nd Ed., Interscience, New York, 1950. Solubility under 0.1% is preferred for suspension concentrates; solution concentrates are preferably stable against phase separation at 0° C. "McCutcheon's Detergents and Emulsifiers Annual", MC Publishing Corp., Ridgewood, New Jersey, as well as Sisely and Wood, "Encyclopedia of Surface Active Agents", Chemical Publishing Co., Inc., New York, 1964, list surfactants and recommended uses. All formulations can contain minor amounts of additives to reduce foaming, caking, corrosion, microbiological growth, etc.

The methods of making such compositions are well known. Solutions are prepared by simply mixing the ingredients. Fine solid compositions are made by blending and, usually, grinding as in a hammer or fluid energy mill. Suspensions are prepared by wet milling (see, for example, Littler, U.S. Pat. No. 3,060,084). Granules and pellets may be made by spraying the active material on preformed granular carriers or by any one of a number of agglomeration techniques.

Azido compounds (Formula II) can be shock sensitive to varying degrees. In general, they should be processed in such ways that impact (as in fine grinding) is avoided unless the compound and the procedure have been carefully evaluated for safety. Liquid and very dilute solid formulations are preferred for such compounds.

The following examples further illustrate formulations which contain the compounds of this invention as active ingredient. Unless indicated otherwise, all parts are by weight.

EXAMPLE 9

Wettable Powder 1-(4-chlorophenoxy)-3,3-dimethyl-1-(1H-1,2,4-triazol-1-yl)-2-butanol, ester with 2-(methoxycarbonylamino)-1H-benzimidazole-1-carboxylic acid: 30%
synthetic fine silica: 64%
dioctyl sodium sulfosuccinate: 2%
sodium ligninsulfonate: 3%
low-viscosity methyl cellulose: 1%

The ingredients can be combined in a blender of the type which will provide shear, such as a sigma arm mixer. When mixing is complete, the material can be passed through an air mill to provide an average particle size of about 5 μm or less. The product can then be blended, sifted and packed out.

All compounds of Formula (I) can be formulated in the same manner.

EXAMPLE 10

Wettable Powder 1-(1,1'-biphenyl-4-yloxy)-3,3-dimethyl-1-(1H-1,2,4-triazol-1-yl)-2-butanol, ester with 2-(methoxycarbonylamino)-1H-benzimidazole-1-carboxylic acid: 80%
sodium alkylnaphthalenesulfonate: 3%
low-viscosity methyl cellulose: 1%
sucrose: 16%

The ingredients can be blended in a ribbon blender and passed through an air mill to provide an average particle size under 7 microns, reblended, sifted and packaged.

EXAMPLE 11

Wettable Powder 1-(2,4-dichlorophenyl)-4,4-dimethyl-2-(1H-1,2,4-triazol-1-yl)-3-pentanol, ester with 2-(methoxycarbonylamino)-1H-benzimidazole-1-carboxylic acid: 65%
sodium alkylnaphthalenesulfonate: 3%
sodium N-methyl-N-oleyltaurate: 2%
starch: 30%

The ingredients are blended, air-milled, reblended, sifted and packaged.

EXAMPLE 12

Dust 1-(4-azidophenoxy)-3,3-dimethyl-1-(1H-1,2,4-triazol-1-yl)-2-butanone: 5%
powdered sericite: 95%

The active ingredient is dissolved in 3 parts dichloromethane and sprayed upon the carrier in a blender, the solvent is allowed to evaporate, and the product packaged for use.

EXAMPLE 13

Emulsifiable Concentrate 1-(4-azidophenoxy)-3,3-dimethyl-1-(1H-1,2,4-triazol-1-yl)-2-butanol: 30%
sorbitan monostearate and polyoxyethylene condensates: 6%
xylene: 64%

EXAMPLE 14

Dust 1-(1,1'-biphenyl-4-yloxy)-3,3-dimethyl-1-(1H-1,2,4-triazol-1-yl)-2-butanol, ester with 2-(methoxycarbonylamino)-1H-benzimidazole-1-carboxylic acid: 5%
attapulgite: 35%
powdered pyrophyllite: 60%

The active ingredient can be blended with attapulgite and passed through a hammer mill to produce a fine powder substantially all below 200 μm. The ground concentrate can then be blended with powdered pyrophyllite to produce a dust.

EXAMPLE 15

Emulsifiable Concentrate 1-(2,4-dichlorophenyl)-4,4-dimethyl-2-(1H-1,2,4-triazol-1-yl)-3-pentanol, ester with 2-(methoxycarbonylamino)-1H-benzimidazole-1-carboxylic acid: 15%
blend of oil-soluble sulfonates and polyoxyethylene ethers: 10%
aromatic hydrocarbon solvent, flash point 41° C.: 75%

The ingredients can be combined and stirred to produce a solution which can be readily emulsified in water for application or can be directly applied.

EXAMPLE 16

Oil Suspension 1-(4-chlorophenoxy)-3,3-dimethyl-1-(1H-1,2,4-triazol-1-yl)-1-buten-2-ol, ester with 2-(methoxycarbonylamino)-1H-benzimidazole-1-carboxylic acid: 25% polyoxyethylene sorbitol hexaoleate: 5%
highly aliphatic hydrocarbon oil, visc. ca. 200 cps.: 70%

The ingredients are combined and ground together in a sand mill until the solid particles average below 5 μm diameter. The resulting suspension can be applied directly, but preferably after being extended with oils or water.

EXAMPLE 17

Solution 1-(4-azidophenoxy)-3,3-dimethyl-1-(1H-1,2,4-triazol-1-yl)-2-butanol, ester with 2-(methoxycarbonylamino)-1H-benzimidazole-1-carboxylic acid: 20%
isophorone: 60%
corn oil: 20%

The ingredients are combined to produce a solution for ULV spraying.

Utility

The compounds of this invention are useful as plant disease control agents. They are effective in controlling a broad spectrum of plant diseases, particularly foliar pathogens of ornamental, vegetable, cereal and fruit crops, such as *Puccinia graminis* var. tritici, *Erysiphe cichoracearum, Venturia inaequalis* and *Pyricularia oryzae,* and *Cercospora arachidicola.* In addition, they protect seed from many soil-borne and seed-borne pathogens.

Disease control is ordinarily accomplished by applying an effective amount of the compound to the portion of the plant to be protected, such as the roots, stems, foliage, fruit, seeds, tubers or bulbs, or to the media (soil or sand) in which the plants to be protected are growing. The compound can also be applied to the seed from which the plants to be protected are to be grown.

Rates of application for these compounds can be influenced by many factors of the environment and should be determined under actual use conditions. Foliage can normally be protected when treated at a rate of from less than 1 to 500 ppm of active ingredient. Plants growing in soil treated at a concentration of from 0.1 to about 20 kg/ha can be protected from disease. Seed and seedlings can normally be protected when the seed is treated at a rate of from 0.06 to about 3 grams per kilogram of seed.

The compounds of this invention can be mixed with fungicides, bactericides, acaricides, nematicides, insecticides, or other biologically active compounds in order to achieve desired results with a minimum expenditure of time, effort and material. Amounts of these biologically active materials added for each part by weight of the composition of this invention may vary from 0.05 to 25 parts by weight. Suitable agents of this type are well-known to those skilled in the art. Some are listed below:

Fungicides methyl 2-benzimidazolecarbamate (carbendazim)
tetramethylthiuram disufide (thiram)
n-dodecylguanidine acetate (dodine)
manganese ethylenebisdithiocarbamate (maneb)
1,4-dichloro-1,5-dimethyoxybenzene (chloroneb)
methyl 1-(butylcarbamoyl)2-benzimidazolecarbamate (benomyl)
2-cyano-N-ethylcarbamoyl-2-methoxyiminoacetamide "Curzate"
N-(trichloromethylthio)tetrahydrophthalimide (captan)
N-(trichloromethylthio)phthalimide (folpet)

Bactericides tribasic copper sulfate
streptomycin sulfate

Acaracides senecioic acid, ester with 2-sec-butyl-4,6-dinitrophenol ("Morocide")
6-methyl-1,3-dithiolo[4,5-B]quinoxalin-2-one ("Morestan")
2,2,2-trichloro-1,1-bis(4-chlorophenyl)ethanol ("Kelthane")
bis(pentachloro-2,4-cyclopentadien-1-yl)("Pentac")
tricyclohexyltin hydroxide ("Plictran")

Nematicides p1

2-[diethoxyphosphinylimino]-1,3-dithietane ("Nematak") S-methyl 1-(dimethylcarbamoyl)-N-(methylcarbamoyloxy)-thioformimidate (oxamyl)
S-methyl 1-carbamoyl-N-(methylcarbamoyloxy)thioformidate
N-isopropylphosphoramidic acid, O-ethyl-O'[4-(methylthio)-m-tolyl]diester ("Nemacur")

Insecticides 3-hydroxy-N-methylcrotonamide, dimethyl phosphate ester ("Azodrin")
methylcarbamic acid, ester with 2,3-dihydro-2,2-dimethyl-7-benzofuranol ("Furadan")
O-[2,4,5-trichloro-α-(chloromethyl)benzyl]phosphoric acid, O', O'-dimethyl ester ("Gardona")
2-mercaptosuccinic acid, diethyl ester, S-ester with thionophosphoric acid, dimethyl ester ("Malathion")
phosphorothioic acid, O,O-dimethyl, O-p-nitrophenyl ester (methyl parathion)
methylcarbamic acid, ester with α-naphthol ("Sevin")
methyl N-[[(methylamino)carbonyl]oxy]ethanimidothioate (methomyl)
N'-(4-chloro-o-tolyl)-N,N-dimethylformamidine ("Galecron")
O,O-diethyl O-(2-isopropyl-4-methyl-6-pyrimidyl)-phosphorothioate) ("Diazinon")
octachlorocamphene (toxaphene)
O-ethyl O-p-nitrophenyl phenylphosphonothioate (EPN)
cyano(3-phenoxyphenyl)methyl 4-chloro-α-(1-methyl-ethyl)benzeneacetate ("Pydrin")
(3-phenoxyphenyl)methyl (±)-cis,trans-3-(2,2-dichloroethenyl)2,2-dimethylcyclopropanecarboxylate ("Ambush")
dimethyl N,N'-[thiobis[(N-methylimino)carbonyloxy]]-bis[ethanimidothioate] ("Larvin")
O-(4-bromo-2-chlorophenyl) O-ethyl S-propyl phosphorothioate ("Curacron")
O-ethyl O-[4-(methylthio)phenyl] S-propyl phosphorodithioate ("Bolstar")

This invention is further illustrated by the following examples.

EXAMPLE 18

A compound of this invention was dissolved in acetone in an amount equal to 6% of the final volume and then suspended at a concentration of 100 ppm in purified water containing 250 ppm of the surfactant TREM 014 (polyhydric alcohol esters). This suspension was sprayed to the point of run-off on apple seedlings. The following day, the plants were inoculated with a spore suspension of the fungus *Venturia inaequalis* and incubated in a saturated humidity chamber at 20° C. for 24 hours and then in a growth room for an additional 10–12 days. Disease ratings were then made and recorded as shown in the following table.

TABLE 4

| Compound | % Control Apple Scab Benomyl-Tolerant | 100 ppm Apple Scab Benomyl-Sensitive Multi-Purpose Confirmatory |
|---|---|---|
| 1-(4-chlorophenoxy)-3,3-dimethyl-1-(1H-1,2,4-triazol-1-yl)-2-butanol, ester with 2-(methoxycarbonylamino)-1H-benzimidazole-1-carboxylic acid | 100 | 100 (1G) |
| 1-(4-azidophenoxy)-3,3-dimethyl 1-(1H-1,2,4-triazol-1-yl)-2-butanone | 0 | 60 |
| 1-(4-chlorophenoxy)-3,3-dimethyl-1-(1H-1,2,4-triazol-1-yl)-1-buten-2-ol, ester with 2-(methoxycarbonylamino)-1H-benzimidazole-1-carboxylic acid | 60 | 98 |
| 1-(1,1'-biphenyl-4-yloxy)-3,3-dimethyl-1-(1H-1,2,4-triazol-1-yl)-2-butanol, ester with 2-(methoxycarbonylamino)-1H-benzimidazole-1-carboxylic acid | 30 | 100 |
| 1-(2,4-dichlorophenyl)-4,4-dimethyl-2-(1H-1,2,4-triazol-1-yl)-3-pentanol, ester with 2-(methoxycarbonylamino)-1H-benzimidazole-1-carboxylic acid | 30 | 100 (8G) |
| 1-(4-azidophenoxy)-3,3-dimethyl-1-(1H-1,2,4-triazol-1-yl)-2-butanol | 80 | 99 |
| 1-(4-azidophenoxy)-3,3-dimethyl-1-(1H-1,2,4-triazol-1-yl)-2-butanol, ester with 2-(methoxycarbonylamino)-1H-benzimidazole-1-carboxylic acid | 0 | 99 |

EXAMPLE 19

A compound of this invention was dissolved in acetone in an amount equal to 6% of the final volume and then suspended at a concentration of 100 ppm in purified water containing 250 ppm of the surfactant TREM 014 (polyhydric alcohol esters). This suspension was sprayed to the point of run-off on peanut seedlings. The following day, the plants were inoculated with a spore suspension of *Cercospora arachidicola* and incubated in a saturated humidity chamber at 27° for 24 hours and then in a growth room for an additional 14 days, when disease ratings were made. The results are shown in the following table. Treated plants had significantly fewer leafspots whereas the untreated plants had numerous leafspots on inoculated leaves. Hormonal effect in the form of growth reduction and/or leaf greening was observed on some of the plants in association with disease control.

TABLE 5

| Compound | 100 ppm % Control Peanut Leafspot | 100 ppm Peanut Leafspot Multi-Purpose Confirmatory |
|---|---|---|
| 1-(4-chlorophenoxy)-3,3-dimethyl-1-(1H-1,2,4-triazol-1-yl)-2-butanol, ester with 2-(methoxycarbonylamino)-1H-benzimidazole-1-carboxylic acid | 100 (G)* | 100 |
| 1-(4-azidophenoxy)-3,3-dimethyl 1-(1H-1,2,4-triazol-1-yl)-2-butanone | 80 | 90 |
| 1-(4-chlorophenoxy)-3,3-dimethyl-1-(1H-1,2,4-triazol-1-yl)-1-buten-2-ol, ester with 2-(methoxycarbonylamino)-1H-benzimidazole-1-carboxylic acid | 100 | 100 |
| 1-(1,1'-biphenyl-4-yloxy)-3,3-dimethyl-1-(1H-1,2,4-triazol-1-yl)-2-butanol, ester with 2-(methoxycarbonylamino)-1H-benzimidazole-1-carboxylic acid | 100 | 100 |
| 1-(2,4-dichlorophenyl)-4,4-dimethyl-1-(1H-1,2,4-triazol-1-yl)-3-pentanol, ester with 2-(methoxycarbonylamino)-1H-benzimidazole-1-carboxylic acid | 100 | 100 |
| 1-(4-azidophenoxy)-3,3-dimthy-1-(1H-1,2,4-triazol-1-yl)-2-butanol | 100 | 30 |
| 1-(4-azidophenoxy)-3,3-dimethyl-1-(1H-1,2,4-triazol-1-yl)-2-butanol, ester with 2-(methoxycarbonylamino)-1H-benzimidazole-1-carboxylic acid | 100 | 95 |

*G = growth reduction

EXAMPLE 20

The compound prepared in Example 6 was dissolved in acetone in an amount equal to 6% of the final volume and then suspended at a concentration of 100 ppm in purified water containing 250 ppm of the surfactant TREM 014 (polyhydric alcohol esters). This suspension was sprayed to the point of run-off on rice seedlings. The following day, the plants were inoculated with a spore suspension of *Pyricularia oryzae* and incubated in a saturated humidity chamber at 20° C. for 24 hours and then in a growth room for an additional 7 days when disease ratings were made. Percent disease control is shown in the following table.

TABLE 6

| Compound | 100 ppm % Control Rice Blast | 100 ppm Rice Blast Multi-Purpose Confirmatory |
|---|---|---|
| 1-(4-chlorophenoxy)-3,3-dimethyl-1-(1H-1,2,4-triazol-1-yl)-2-butanol, ester with 2-(methoxycarbonylamino)-1H-benzimidazole-1-carboxylic acid | 70 | 0 |
| 1-(4-azidophenoxy)-3,3-dimethyl 1-(1H-1,2,4-triazol-1-yl)-2-butanone | 0 | 0 |
| 1-(4-chlorophenoxy)-3,3-dimethyl-1-(1H-1,2,4-triazol-1-yl)-1-buten-2-ol, ester with 2-(methoxycarbonylamino)-1H-benzimidazole-1-carboxylic acid | 0 | 0 |
| 1-(1,1'-biphenyl-4-yloxy)-3,3-dimethyl-1-(1H-1,2,4-triazol-1-yl)-2-butanol, ester with 2-(methoxycarbonylamino)-1H-benzimidazole-1-carboxylic acid | 0 | 0 |
| 1-(2,4-dichlorophenyl)-4,4-dimethyl-2-(1H-1,2,4-triazol-1-yl)-3-pentanol, ester with 2-(methoxycarbonylamino)-1H-benzimidazole-1-carboxylic acid | 0 | 0 |
| 1-(4-azidophenoxy)-3,3-dimethyl-1-(1H-1,2,4-triazol-1-yl)-2-butanol | 0 | 0 |
| 1-(4-azidophenoxy)-3,3-dimethyl-1-(1H-1,2,4-triazol-1-yl)-2-butanol, ester with 2-(methoxycarbonylamino)-1H-benzimidazole-1-carboxylic acid | 0 | 0 |

EXAMPLE 21

A compound of the previous example was again dissolved in acetone in an amount equal to 6% of the final volume and then suspended at a concentration of 100 ppm in purified water containing 250 ppm of the surfactant TREM 014 (polyhydric alcohol esters). This suspension was sprayed to the point of run-off on wheat seedlings. The following day, the plants were inoculated with a spore suspension of *Puccinia graminis* var. *tritici* and incubated in a saturated humidity chamber at 20° for 24 days and then in a growth room for an additional 7 days, when disease ratings were made. Percent disease control is shown in the following table.

TABLE 7

| Compound | 100 ppm % Control Wheat Rust | 100 ppm Wheat Rust Multi-Purpose Confirmatory |
|---|---|---|
| 1-(4-chlorophenoxy)-3,3-dimethyl-1-(1H-1,2,4-triazol-1-yl)-2-butanol, ester with 2-(methoxycarbonylamino)-1H-benzimidazole-1-carboxylic acid | 100 | 100 |
| 1-(4-azidophenoxy)-3,3,-dimethyl 1-(1H-1,2,4-triazol-1-yl)-2-butanone | 100 | 100 |
| 1-(4-chlorophenoxy)-3,3-dimethyl-1-(1H-1,2,4-triazol-1-yl)-1-buten-2-ol, ester with 2-(methoxycarbonylamino)-1H-benzimidazole-1-carboxylic acid | 100 (B)* | 100 |
| 1-(1,1'-biphenyl-4-yloxy)-3,3-dimethyl-1-(1H-1,2,4-triazol-1-yl)-2-butanol, ester with 2-(methoxycarbonylamino)-1H-benzimidazole-1-carboxylic acid | 0 | 90 |
| 1-(2,4-dichlorophenyl)-4,4-dimethyl-2-(1H-1,2,4-triazol-1-yl)-3-pentanol, ester with 2-(methoxycarbonylamino)-1H-benzimidazole-1-carboxylic acid | 100 | 100 |
| 1-(4-azidophenoxy)-3,3-dimethyl-1-(1H-1,2,4-triazol-1-yl)-2-butanol | 100 | 100 |
| 1-(4-azidophenoxy)-3,3-dimethyl-1-(1H-1,2,4-triazol-1-yl)-2-butanol, ester with 2-(methoxycarbonylamino)-1H-benzimidazole-1-carboxylic acid | 100 | 100 |

*B = Burn

EXAMPLE 22

A compound of the previous example was again dissolved in acetone in an amount equal to 6% of the final volume and then suspended at a concentration of 100 ppm in purified water containing 250 ppm of the surfactant TREM 014 (polyhydric alcohol esters). This suspension was sprayed to the point of run-off on cucumber seedlings. The following day, the plants were inoculated with a spore suspension of the fungus *Erysiphe cichoracearum* and incubated in a growth room for 7 days. Disease ratings were then made. Percent disease control is shown in the following table. Treated plants had no powdery mildew in contrast to untreated plants which were covered with powdery mildew. Phytotoxicity in the form of growth reduction was observed on some of the plants in association with disease control.

TABLE 8

| Compound | 100 ppm % Control Cucumber Powdery Mildew |
|---|---|
| 1-(4-chlorophenoxy)-3,3-dimethyl-1-(1H-1,2,4-triazol-1-yl)-2-butanol, ester with 2-(methoxycarbonylamino)-1H-benzimidazole-1-carboxylic acid | 100 *(G) |
| 1-(4-azidophenoxy)-3,3-dimethyl 1-(1H-1,2,4-triazol-1-yl)-2-butanone | 100 |
| 1-(4-chlorophenoxy)-3,3-dimethyl-1-(1H-1,2,4-triazol-1-yl)-1-buten-2-ol, ester with 2-(methoxycarbonylamino)-1H-benzimidazole-1-carboxylic acid | 100 *(G) |
| 1-(1,1'-biphenyl-4-yloxy)-3,3-dimethyl-1-(1H-1,2,4-triazol-1-yl)-2-butanol, ester with 2-(methoxycarbonylamino)-1H-benzimidazole-1-carboxylic acid | 100 |
| 1-(2,4-dichlorophenyl)-4,4-dimethyl-2-(1H-1,2,4-triazol-1-yl)-3-pentanol, ester with 2-(methoxycarbonylamino)-1H-benzimidazole-1-carboxylic acid | 100 *(G) |
| 1-(4-azidophenoxy)-3,3-dimethyl-1-(1H-1,2,4-triazol-1-yl)-2-butanol | 100 |
| 1-(4-azidophenoxy)-3,3-dimethyl-1-(1H-1,2,4-triazol-1-yl)-2-butanol, ester with 2-(methoxycarbonylamino)-1H-benzimidazole-1-carboxylic acid | 100 |

*B = Burn

EXAMPLE 23

Seeds of crabgrass (*Digitaria* spp.), barnyardgrass (*Echinochloa crusgalli*), wild oats (*Avena fatua*), Cassia tora, mornigglory (*Ipomoea* spp.), cocklebur (*Xanthium* spp.), sorghum, corn, soybean, rice, wheat and nutsedge tubers were planted in a growth medium and treated pre-emergence with 1-(2-4-dichlorophenyl)-4,4-dimethyl-2-(1H-1,2,4-triazol-1-yl)-3-pentanol, ester with 2-(methoxycarbonylamino)-1H-benzimidazole-1-carboxylic acid (I)c in a non-phytotoxic solvent. At the same time, cotton having five leaves (including cotyledonary ones), bush beans with the second trifoliate leaf expanding, crabgrass with two leaves, barnyardgrass with two leaves, wild oats with one leaf, cassia with three leaves (including cotyledonary ones), morningglory with four leaves (including the cotyledonary ones), cocklebur with four leaves (including the cotyledonary ones), sorghum with three leaves, corn with three leaves, soybean with two cotyledonary leaves, rice with two leaves, wheat with two leaves, and nutsedge with three-five leaves were sprayed. Treated plants and controls were maintained in a greenhouse for fifteen days, then all species were compared to controls and visually rated for response to treatment. The plant response data are presented in Table 9.

The ratings are based on a numerical scale extending from 0=no injury, to 10=complete kill. The accompanying descriptive symbols have the following meanings:

G = growth retardation;
I = Increased chlorophyll (darker green than control);
%Z = Fasciation; and
6Y = Abscised buds or flowers.

The data in Table 9 indicate that the compound has plant-growth-regulant activity including retarding the growth of vegetation, enhancing green color, leaf expansion on grasses and effects on flowering and fruit set. Examination of the bush bean plants showed an increase in root mass compared to an untreated check.

The plants were excised at the soil line and the roots washed free of soil. The fresh weight of the tops and roots were determined. The tops and roots were then placed in a drying oven at 100° F. for 24 hours. The dry weight of the tops and roots were determined. The data are presented in Table 9.

TABLE 9

Plant Response Ratings Fifteen Days After Treatment

| | Rate 2 kg/ha | |
|---|---|---|
| Test Plant | Post-Emergence | Pre-Emergence |
| Bush bean | 8G, 5I, 6Y | |
| Cotton | 9G, 5I | |
| Morningglory | 2G | 9G, 5I |
| Cocklebur | 0 | 8G |
| Cassia | 4G | 8G, 5I |
| Nutsedge | 2G | 7G |
| Crabgrass | 4G | 5G |
| Barnyardgrass | 5G, % Z | 8G, % Z |
| Wild oats | 2G | 8G |
| Wheat | 2G | 8G |
| Corn | 5G | 6G |
| Soybean | 5G, 5I | 9G, 5I |
| Rice | 4G | 7G |
| Sorghum | 0 | 6G |

TABLE 10

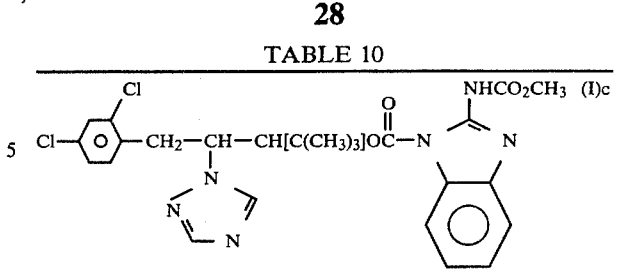

Compound (I)c

| | | Wt. of Roots (gms) | | Wt. of Tops (gms) (Vegetation & Fruit) | |
|---|---|---|---|---|---|
| Treatment | Rate, kg/ha | Fresh | Dry | Fresh | Dry |
| Treated | 2 | 27.6 | 2.45 | 47.7 | 5.45 |
| Control | — | 16.5 | 1.82 | 71.6 | 8.12 |

What is claimed is:

1. A compound of the formula:

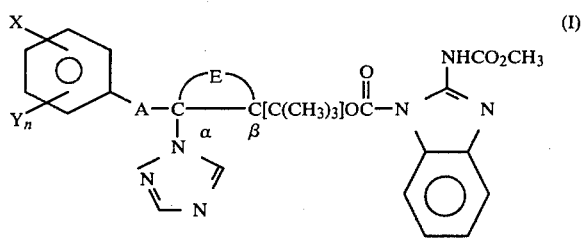

wherein
A is O or CH$_2$;
X is hydrogen, halogen, cyano, alkyl (C$_1$–C$_4$), alkoxy (C$_1$–C$_4$), haloalkoxy (C$_1$–C$_3$, 2–6 halogens), alkylthio (C$_1$–C$_4$), trifluoromethyl, alkylsulfonyl (C$_1$–C$_4$), trifluoromethanesulfonyl, phenyl, 2- or 4-halophenyl, or azido;
Y is halogen;
n is 0 to 1 and can be 0 to 2 when X is halogen; and
E is a hydrogen atom on each of carbons α and β, or can be a bond when A is oxygen.

2. A compound of claim 1 in which X is hydrogen, halogen, methyl, methoxy, trifluoromethyl or phenyl.

3. A compound of claim 1 which is 1-(4-chlorophenoxy)-3,3-dimethyl-1-(1H-1,2,4-triazol-1-yl)-2-butanol, ester with 2-(methoxycarbonylamino)-1H-benzimidazole-1-carboxylic acid.

4. A compound of claim 1 which is 1-(1,1'-biphenyl-4-yloxy)-3,3-dimethyl-1-(1H-1,2,4-triazol-1-yl)-2-butanol, ester with 2-(methoxycarbonylamino-1H-benzimidazole-1-carboxylic acid.

5. A compound of claim 1 which is 1-(2,4-dichlorophenyl)-4,4-dimethyl-2-(1H-1,2,4-triazol-1-yl)-3-pentanol, ester with 2-(methoxycarbonylamino)-1H-benzimidazole-1-carboxylic acid.

6. A compound of claim 1 which is 1-(4-chlorophenoxy)-3,3-dimethyl-1-(1H-1,2,4-triazol-1-yl)-1-buten-2-ol, ester with 2-(methoxycarbonylamino)-1H-benzimidazole-1-carboxylic acid.

7. A compound of claim 1 which is 1-(1,1'-biphenyl-4-yloxy)-3,3-dimethyl-1-(1H-1,2,4-triazol-1-yl)-1-buten-2-ol, ester with 2-(methoxycarbonylamino)-1H-benzimidazole-1-carboxylic acid.

8. A compound of claim 1 which is 1-(4-azidophenoxy)-3,3-dimethyl-1-(1H-1,2,4-triazol-1-yl)-2-butanol, ester with 2-(methoxycarbonylamino)-1H-benzimidazole-1-carboxylic acid.

9. A composition consisting essentially of an effective amount of a compound of claim 1 and at least one of (a) about 0% to 20% by weight surfactant(s) and (b) from about 1% to 99.9% by weight solid or liquid inert diluent(s).

10. A composition consisting essentially of an effective amount of a compound of claim 2 and at least one of (a) about 0% to 20% by weight surfactant(s) and (b) from about 1% to 99.9% by weight solid or liquid inert diluent(s).

11. A composition consisting essentially of an effective amount of a compound of claim 3 and at least one of (a) about 0% to 20% by weight surfactant(s) and (b) from about 1% to 99.9% by weight solid or liquid inert diluent(s).

12. A composition consisting essentially of an effective amount of a compound of claim 4 and at least one of (a) about 0% to 20% by weight surfactant(s) and (b) from about 1% to 99.9% by weight solid or liquid inert diluent(s).

13. A composition consisting essentially of an effective amount of a compound of claim 5 and at least one of (a) about 0% to 20% by weight surfactant(s) and (b) from about 1% to 99.9% by weight solid or liquid inert diluent(s).

14. A composition consisting essentially of an effective amount of a compound of claim 6 and at least one of (a) about 0% to 20% by weight surfactant(s) and (b) from about 1% to 99.9% by weight solid or liquid inert diluent(s).

15. A composition consisting essentially of an effective amount of a compound of claim 7 and at least one of (a) about 0% to 20% by weight surfactant(s) and (b) from about 1% to 99.9% by weight solid or liquid inert diluent(s).

16. A composition consisting essentially of an effective amount of a compound of claim 8 and at least one of (a) about 0% to 20% by weight surfactant(s) and (b) from about 1% to 99.9% by weight solid or liquid inert diluent(s).

17. A method for controlling fungus diseases in plants comprising applying to the locus to be protected an effective amount of the compound of claim 1.

18. A method for controlling fungus diseases in plants comprising applying to the locus to be protected an effective amount of the compound of claim 2.

19. A method for controlling fungus diseases in plants comprising applying to the locus to be protected an effective amount of the compound of claim 3.

20. A method for controlling fungus diseases in plants comprising applying to the locus to be protected an effective amount of the compound of claim 4.

21. A method of controlling fungus diseases in or regulating the growth of a plant comprising applying to the plant, to seed of the plant or to the locus of the plant or seed an effective amount of the compound of claim 5.

22. A method for controlling fungus diseases in plants comprising applying to the locus to be protected an effective amount of the compound of claim 6.

23. A method for controlling fungus diseases in plants comprising applying to the locus to be protected an effective amount of the compound of claim 7.

24. A method for controlling fungus diseases in plants comprising applying to the locus to be protected an effective amount of the compound of claim 8.

* * * * *